United States Patent [19]

Foslien

[11] Patent Number: 5,379,895

[45] Date of Patent: Jan. 10, 1995

[54] PACKAGE FOR SURGICAL DEVICE

[75] Inventor: Floyd L. Foslien, Troy, Wis.

[73] Assignee: Minnesota Mining and Manufacturing Company, St. Paul, Minn.

[21] Appl. No.: 203,702

[22] Filed: Feb. 28, 1994

Related U.S. Application Data

[63] Continuation of Ser. No. 120,296, Sep. 13, 1993, abandoned.

[51] Int. Cl.⁶ .......................................... B65D 81/02
[52] U.S. Cl. .................... 206/363; 206/461; 206/523; 206/814
[58] Field of Search .............................. 206/363–370, 206/461, 467–471, 438, 523, 814

[56] References Cited

U.S. PATENT DOCUMENTS

| | | | |
|---|---|---|---|
| 3,013,656 | 12/1961 | Murphy, Jr. . | |
| 3,035,691 | 5/1962 | Rasmussen et al. | 206/364 |
| 3,138,253 | 6/1964 | Harautuneian | 206/364 |
| 3,301,392 | 1/1967 | Regan, Jr. | 206/438 |
| 3,755,042 | 8/1973 | Robertson et al. | 206/438 |
| 4,128,173 | 12/1978 | Lazarus et al. | 206/570 |
| 4,262,800 | 4/1981 | Nethercutt | 206/364 |
| 4,321,781 | 3/1982 | Hall | 206/471 |
| 4,324,331 | 4/1982 | Ignasiak | 206/363 |
| 4,479,792 | 10/1984 | Lazarus et al. | 604/29 |
| 4,497,406 | 2/1985 | Taknashi | 206/438 |
| 4,511,035 | 4/1985 | Alpern | 206/363 |
| 4,520,817 | 6/1985 | Green | 128/305 |
| 4,573,576 | 3/1986 | Krol | 206/471 |
| 4,730,726 | 3/1988 | Holzwarth | 206/471 |
| 4,917,245 | 4/1990 | Wu | 206/471 |
| 5,133,454 | 7/1992 | Hammer | 206/364 |
| 5,144,942 | 9/1992 | Decarie et al. | 128/4 |
| 5,193,679 | 3/1993 | White | 206/363 |
| 5,197,597 | 3/1993 | Leary et al. | 206/63.3 |
| 5,199,561 | 4/1993 | Roshdy et al. | 206/63.3 |

OTHER PUBLICATIONS

Product Information on Scotchpack ™, Heat Sealable Polyester Film, (1 page).
Techniques for Tyvek ®, Typical Properties of Type 10 Tyvek ® Spunbonded Olefin (English Units), (1 page).
Auto Suture, Multifire GIA 80-4.8 Disposable Surgical Stapler (1 page).

*Primary Examiner*—Jimmy G. Foster
*Attorney, Agent, or Firm*—Gary L. Griswold; Walter N. Kirn; Jeffrey J. Hohenshell

[57] ABSTRACT

A package for a surgical device such as a stapler is described. The package includes a top portion, a bottom portion, sidewalls which define a cavity that receives the stapler, bearing surfaces to abut the stapler and a flexible cover. The package also includes a conformable member situated between the cover and the stapler which deforms about the stapler to hold the stapler relative to the package when the cover is attached to the top portion, and which is released from the stapler when the cover is removed from the top portion.

24 Claims, 4 Drawing Sheets

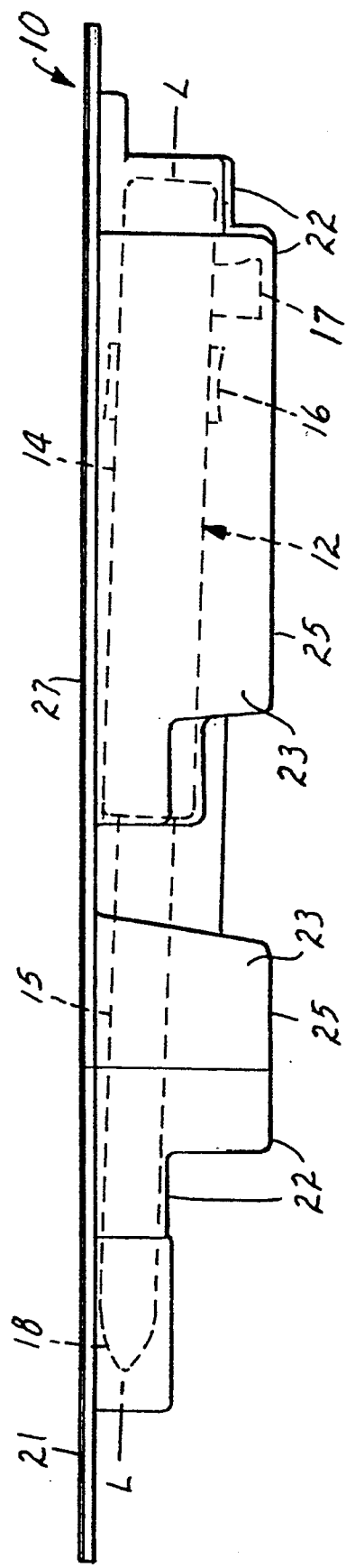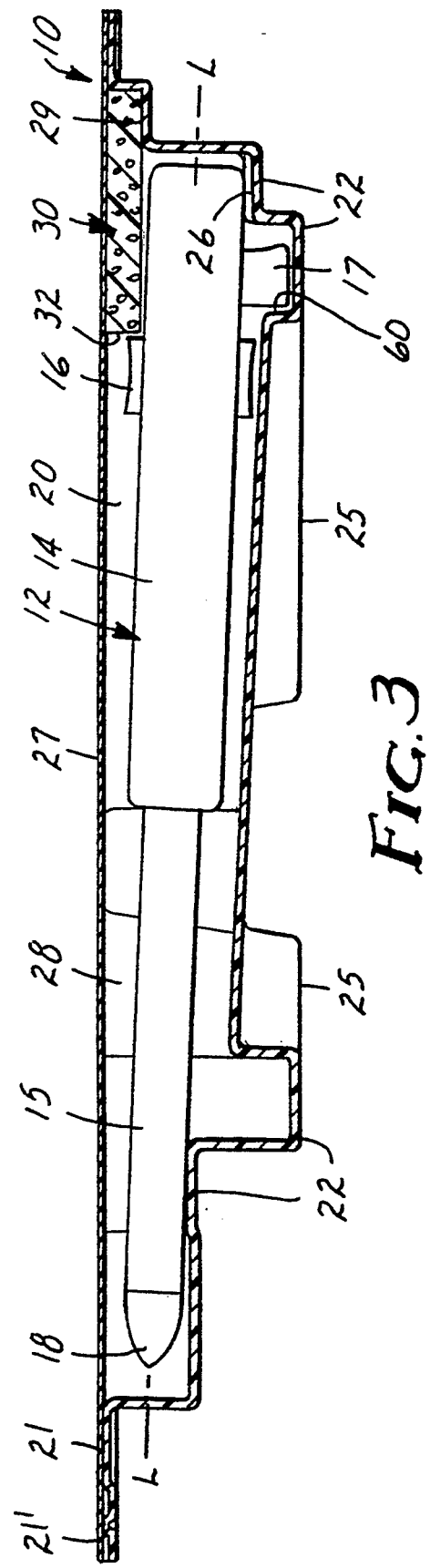

PACKAGE FOR SURGICAL DEVICE

This is a continuation of application No. 08/120,296 filed Sep. 13, 1993, abandoned.

TECHNICAL FIELD

The present invention is directed to a sterilizable package for a surgical device and more particularly to a sterile package for a surgical stapler.

Background

The art is replete with packages for surgical instruments or devices. Examples of packages for surgical devices are shown in U.S. Pat. No.'s 3,013,656, 4,128,173, 4,262,800, 4,324,331, 4,479,792, 4,573,576 and 5,144,942. Typically, but not exclusively, such packages comprise a bottom part and a peelable lid. The lid is attached to the bottom part; and the package may be opened by peeling the lid from the bottom part.

Creating packages for surgical instruments requires attention to several considerations which are not present for ordinary consumer packages of common commodities. Of course, surgical instruments must be sterile before use, and the packages used to transport the instruments should present the instrument to medical personnel in a sterile condition.

Each surgical instrument should be properly protected during transportation from the initial packaging site to the operating room. In this regard, only the highest standards of reliability are acceptable for a surgical instrument, unlike many conventional packaged products. Standards for packages for transporting surgical instruments are also high, commensurate with the high standards of reliability required of the surgical instruments.

The package for a surgical instrument should resist damage from the surgical instrument itself, particularly when an instrument with a sharp surface (such as a trocar or pnuemoneedle) is contained or when an instrument with a relatively large mass (such as an internal surgical stapler) is contained. A further consideration is that each package should afford convenient and efficient access to the surgical instrument so that undue effort and time is not spent in retrieving the instrument from the package. Additionally, when the surgical instrument comprises a device which has movable parts (e.g. such as a stapler, tissue tacker, trocar or clip applier), the package should also ensure the surgical instrument arrives at the operating room in an original condition. For example, if the surgical instrument includes a firing mechanism, such as a stapler, the stapler should arrive at the operating room in an unfired condition. Some prior art even teaches the use of a mechanism or structure in the surgical instrument itself to prevent premature firing of the instrument. Note the stapler described in Green U.S. Pat. No. 4,520,817 at column 12, line 27 to line 55.

Prior art packages for surgical instruments encounter problems in simultaneously addressing all of the above identified considerations. One such prior art package is the package used to transport a Pnuemo-Intestinal "PI" type surgical stapler generally available from Minnesota Mining and Manufacturing Co. (3M) of St. Paul, Minn. and generally described in U.S. patent application No.'s 07/699,718 and 07/699,719 each filed, filed May 14, 1991, and Application No. 07/946,039 filed Sep. 15, 1992 which is a file-wrapper continuation of Application No. 07/699,719) the entire contents of each of which are herein expressly incorporated by reference.

In use, the stapler and package combination is transported to the surgical operating room. To open the package, the cover is peeled from the bottom part of the package. The stapler is then typically removed from the package in one of two manners. First, medical personnel may reach into the bottom part of the package, grasp the jaw portions of the stapler, remove the stapler from the bottom part and present the stapler to the surgeon so that he or she may grasp the handle portion of the stapler. However, this operation jeopardizes contact between the top portion of the package that was previously adhered to the lid (which is considered non-sterile) and medical personnel, with the attendant risks of contamination to the patient.

Second, the package may be inverted in a sterile field or area of the operating room, and the stapler is allowed to drop into the sterile field or area under the influence of gravity. To allow the stapler to be easily removed from the bottom part of the package, the package may be loosely fit about the stapler. However, such a package may fail to provide package seal integrity and may not provide sufficient protection to the surgical instrument itself. For example, some prior art packages include detent or pinching portions for engaging the surgical instrument to prevent its vibration relative to the package and to firmly hold the instrument so that, in the event of an impulsive force (e.g. when a packaged instrument is dropped and hits the floor) the package restricts the chances or severity of a collision between the instrument and package which may damage the instrument or break the sterile barrier provided by the package.

However, as discussed above, when a prior art package includes a pinching or detent portion, medical personnel typically firmly grasp the outer portion of the package which is not considered sterile. Additionally, such packages generally do not allow the instrument to fall from the package under the influence of gravity when the instrument is inverted.

BRIEF DESCRIPTION OF THE INVENTION

According to the present invention there is provided a package for a surgical device which 1) affords easy and convenient access to the surgical device so that medical personnel are not required to firmly grasp portions of the package which are not considered sterile, and so that the package may be inverted to remove the surgical instrument from the package, 2) includes a conformable member which holds the surgical device relative to the package to resist damage to the device or the package resulting from relative movement between the device and the package (such as when the package and device are dropped and hit the floor), 3) is durable to resist compromise of the sterile condition of the surgical instrument; 4) assists in providing a surgical instrument with movable parts (e.g. a firing mechanism) in an original or unfired condition; and 5) is capable of protecting a surgical instrument with a large mass.

According to the present invention, there is provided a sterilizable package for a surgical device such as a stapler. The package comprises top and bottom portions, sidewalls extending between the top portion and the bottom portion which define a cavity adapted to receive the stapler, bearing surfaces adapted to abut the stapler when the stapler is placed in the cavity, a flexible cover releasably attached to the top portion, and adapted to be removed from the top portion by being manually peeled from the top portion to afford access to the stapler, and a conformable member situated between the cover and the stapler which deforms about at least a portion of the stapler to hold the stapler relative to the package when the cover is attached to the top portion, and which is adapted to release from the stapler when the cover is removed from the top portion.

Preferably, the sidewalls have finger well portions generally adjacent handle and jaw portions of the stapler when the stapler is in the cavity to afford convenient access to the stapler. Also preferably, the conformable member comprises a flexible, resilient material capable of being sterilized. More preferably, the conformable member comprises a foam material adapted to deform about the stapler.

Also preferably, the conformable member is attached to the flexible cover so that the conformable member is removed from contact with the stapler when the flexible cover is removed from the top portion. Preferably the cover assembly is then heat sealed to the rest of the package.

The package is preferably free of structure for grasping the stapler (such as a detent portion in the top, bottom and sidewall portions) other than the conformable member so that, when the flexible cover is removed and the package is inverted, the stapler is capable of falling from the cavity under the influence of gravity without requiring shaking of the package or firm manual grasping of the package.

The package is adapted to present the stapler to the user in a convenient manner. The bottom portion of the package has generally planar exterior base surfaces for resting on a horizontal plane such as a table. The bearing surfaces situate the stapler such that its longitudinal axis is inclined relative to base surfaces to facilitate grasping of the jaw portion of the stapler.

The advantages of the package of the present invention have been found to be particularly desirable when packaging a surgical device with a relatively large mass (e.g a device which weighs between about one-quarter (¼) pounds and about one-hundred (100) 6 pounds). More preferably, the package is most desirable for use in packaging a surgical device which comprises movable parts (e.g. such as a trocar, or a firable or actuatable device such as and internal surgical stapler or clip applier). In such instances the package preferably comprises a mechanism for restricting movement of the movable parts.

BRIEF DESCRIPTION OF THE DRAWINGS

The present invention will be further described with reference to the accompanying drawing wherein like reference numerals refer to like parts in the several views, and wherein:

FIG. 2 is an enlarged side view of the package and stapler of FIG. 1 in an assembled, packaged condition and which illustrates the stapler with dashed lines;

FIG. 3 is a side view similar to FIG. 2 showing a conformable member according to the present invention, with portions of the package sectioned to illustrate details, and with the stapler illustrated in solid lines;

DETAILED DESCRIPTION

Figure 1:
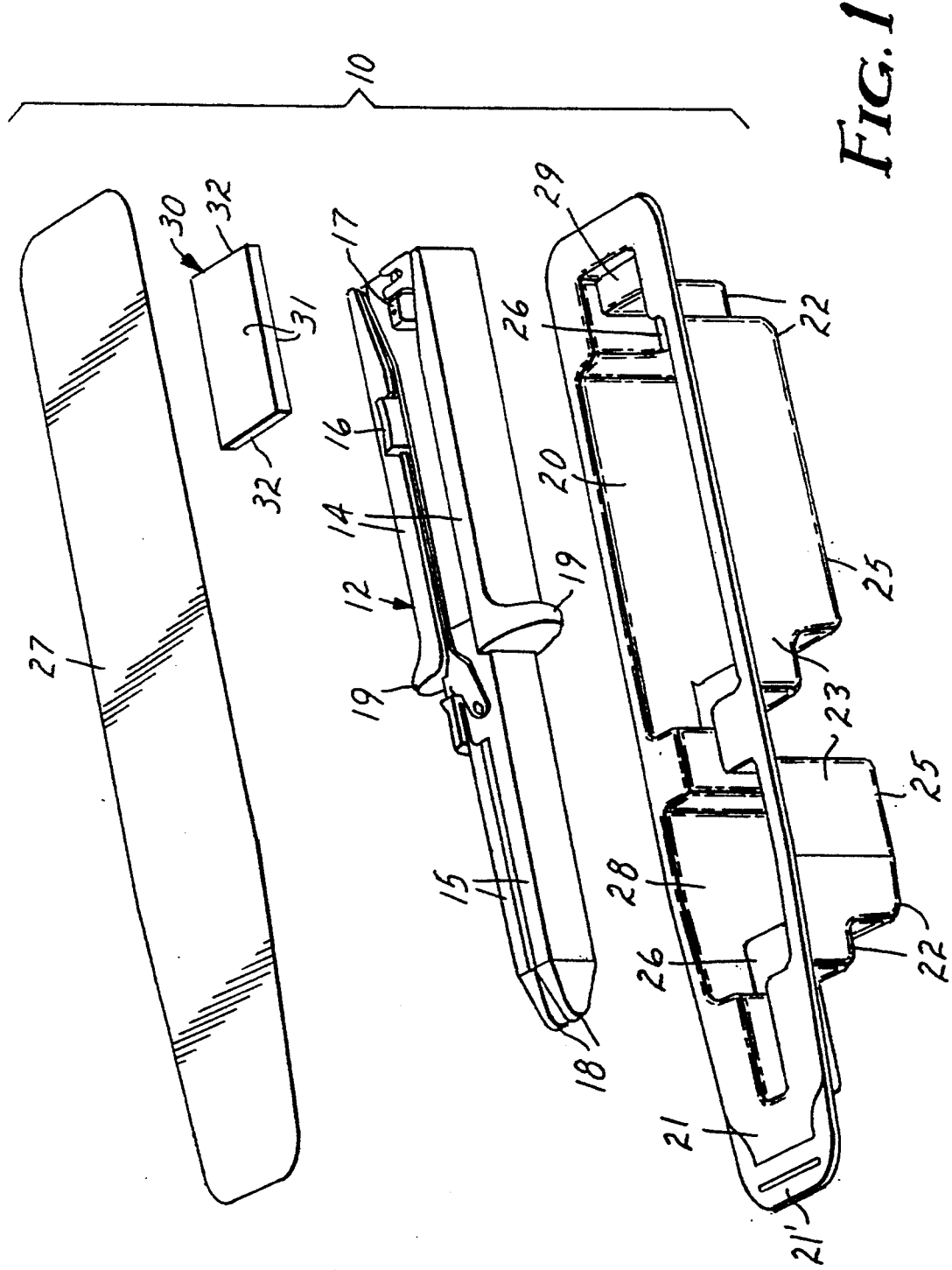
FIG. 1 is an exploded perspective view of a package and surgical stapler according to the present invention.

Referring now to FIGS. 1 through 5 of the drawing there is shown an example of a package according to the present invention generally designated by reference character 10.

The package 10 is designed for use with a surgical device or instrument such as the stapler 12 shown in FIG. 1. As used herein, the phrase "surgical device" or "surgical instrument" is used broadly to encompass a variety of devices used during surgery, such as, but not limited to clip appliers, cannulae, trocars, pneumoneedles, skin staplers, internal staplers, tissue tackers, endoscopes, ligators, forceps, cutters, hemostats, and implantable devices including cardiac pacemakers and acetabular cups. Examples of such surgical instruments are described in U.S. Pat. No.'s 4,535,773, 4,601,710, 4,654,030, 4,902,280, 4,931,042, 5,040,715, 5,084,057, 5,100,420, 5,104,382, 5,116,353, 5,152,754, 5,171,247, 5,171,249 and 5,176,695.

Preferably, the package 10 is designed for use with a surgical device which has a relatively large mass and which includes movable parts. As used herein, the phrase "surgical device with a relatively large mass" means a device between about one-quarter (¼) pounds and about one-hundred (100) pounds, as opposed to, for example, needles, sutures, plastic implants, intra-ocular lenses or other lightweight surgical devices, instruments or implants. The range of less than one-hundred (100) pounds is a range used in step 4 of the Drop Test of Project 1A of the National Safe Transit Association (NSTA) Preshipment Test Procedures (generally available from NSTA at 5940 W. Touhy Avenue, Chicago, Ill., the entire contents of Project 1A of which are herein expressly incorporated by reference). The range is used to distinguish the drop heights of the test.

As used herein, when it is said that the surgical instrument has "movable parts" it is meant that the packaged surgical instrument has at least one part that is relatively movable to another portion of the surgical instrument, e.g. such as the safety trocar shown in U.S. Pat. No. 5,152,754. More particularly, when it is said that the surgical instrument with movable parts comprises a firable surgical instrument, it is meant that the instrument comprises at least one workpiece, such as a staple, clip or tissue tack, that is designed to be separatable from the rest of the surgical instrument during a surgical procedure. The supply of the workpiece in the surgical instrument is exhaustible and at least temporarily used during the surgical procedure.

The surgical device illustrated in the drawings by way of an example is an internal surgical stapler. The stapler 12 comprises the stapler shown and described in U.S. Pat. No.'s 5,083,695 and 5,141,144 the entire contents of which are herein expressly incorporated by reference. The stapler is known generally as the ILA surgical stapler developed by the Minnesota Mining and Manufacturing Company (3M) of St. Paul, Minn. While the package 10 is described in conjunction with the stapler shown in U.S. Pat. No.'s 5,083,695 and 5,141,144, it should be noted that the package 10 may be easily modified for use with other types of surgical staplers including a Proximate ™ PLC75 stapler generally available from Ethicon, Inc. of Sommerville, N.J., or an AutoSuture ™ Multifire ™ GIA disposable surgical stapler, generally available from U.S. Surgical Corporation of Norwalk, Conn., or any of the staplers shown in U.S. Pat. No.'s 4,429,695, 4,520,817, 4,633,861, 4,633,874, 4,892,244, 4,955,959, DES 278,081 or DES 272,851.

The stapler 12 comprises a handle portion 14 and a jaw portion 15. The stapler 12 is elongate and defines an imaginary, central longitudinal axis L (FIGS. 2 and 3) which is discussed below. The outer surfaces of the stapler 12 are irregular and include several discontinuities such as locking buttons 16, grasping wings 19, a generally triangular shaped end portion 18 and a movable firing knob or handle 17.

The attributes of the package 10 are particularly apparent when the surgical instrument comprises a rigid surgical instrument with a relatively large mass (e.g. greater than about one-quarter of a pound (1.11 Newtons) and less than about one-hundred pounds (444.82 Newtons)) with somewhat sharp surfaces (e.g. the end surfaces 18 or the extremely sharp surfaces of a trocar). For example, the stapler 12 is constructed from carbon or stainless steel and thermoplastic materials and weighs about 0.57 pounds (257.25 grams). Although the triangular shaped end 18 of the stapler 12 is generally not sharp enough to puncture skin, the shape of the end 18 of the stapler 12 may be sharp enough to puncture the package 10 or compromise the sterile package 10. Thus, as used in the present application, the relative term "sharp" is used in the context of an object's ability to puncture the package 10. Thus, an otherwise blunt object may be considered sharp when discussing its ability to puncture a package.

The package 10 comprises a top portion 21, a bottom portion 22 recessed from the top portion 21, and sidewalls 23 extending between the top portion 21 and the bottom portion 22 which define a cavity which receives the stapler 12. The bottom portion 22 has generally planar exterior base surfaces 25 for resting on a horizontal plane such as a table (not shown).

The cavity is defined at least in part by the side walls 23 and the bottom portion 22. The cavity preferably includes a finger well portion 28 generally adjacent the jaw portion 15 of the stapler 12, and a finger well portion 20 generally adjacent the handle portion 14 to afford access to the stapler 12. The finger well portions 20 and 28 allow the user to grasp the stapler 12 without touching the top portion 21, the seal area of which is considered non-sterile after the package is opened.

The longitudinal dimension of the cavity is designed to match or to be slightly longer than the longitudinal length of the stapler 12 to restrict excessive fore and aft movement of the stapler 12 relative to the package 10. A middle abutment surface 41 is adapted to abut the grasping wings 19 and an end abutment surface 42 is adapted to abut a proximal portion of the handle portion 14 of the stapler 12 to further resist longitudinal axial movement of stapler 12 relative to the package.

The package 10 also has shoulder surfaces adapted to resist lateral movement of the stapler 12 relative to the package. Lateral movement as used herein means movement in a direction generally perpendicular to the longitudinal axis of the package. For example, the package 10 includes distal end shoulder surface 53 adapted to abut the jaw portion 15 of the stapler 12 and proximal end shoulder surface 52 adapted to abut a proximal end of the handle portion 14 of the stapler 12.

Bottom tray surface 59 is capable of abutting an adjacent lid when a plurality of packages 10 are stacked one on top of another. The bottom tray surface 59 is believed to help keep the stapler in an adjacent tray from moving up between finger well areas and tearing a lid in the process.

The stapler 12 includes a plurality of staples which are designed to be generally sequentially formed in a plurality of parallel rows in tissue during a linear, longitudinal firing stroke of the firing knob 17 of the stapler 10 during a surgical procedure. Optionally, the stapler may include a knife which will cut between the sealed tissue between the parallel rows of formed staples. As best seen in FIG. 3, the sidewalls of the package 10 also include a means for preventing the stapler 12 from prematurely firing during shipping. The sidewalls preferably include a barrier surface 60 which restricts the chances that the firing knob 17 of the stapler 12 will move longitudinally toward the jaw portion 15 during shipping. In this manner, the package 10 restricts the chances that the stapler 12 will prematurely fire during shipping. Engagement between the conformable member 30 and the firing knob 17 biases the firing knob 17 into a well defined in part by the barrier surface 60 which is believed to further assist in preventing the stapler 12 from prematurely firing.

The top 21 and bottom 22 portions and the sidewalls 23 are preferably constructed using any suitable, thermoformable or thermoplastic material suitable for medical purposes. For example, a flat, generally rectangular sheet (e.g. of KODAR TM PETG Copolyester 6763 generally available from Eastman Kodak Company of Kingsport, Tenn.) may be used in conjunction with known heating and vacuum forming techniques to construct the top 21 and bottom 22 portions and the sidewalls 23 in an integral, monolithic structure. Preferably the material used to construct the top 21 and bottom 22 portions and the sidewalls 23 is transparent or substantially transparent. High Density Polyethylene, Polycarbonate Lexan TM GE Corporation; XT 375–301 Polymer-Polyester generally available from Cyro Corporation are alternative materials which may be thermoformed into the tray of the package of the present invention.

The package 10 also includes bearing surfaces 26 which abut the stapler 10. The bearing surfaces 26 are designed to present the stapler 12 such that the longitudinal axis L of the stapler 12 is inclined at an acute included angle relative to base surfaces 25 to facilitate grasping of the jaw portion 15 of the stapler. The bearing surfaces 26 help present the stapler 12 to the user in a convenient manner.

Figure 4:
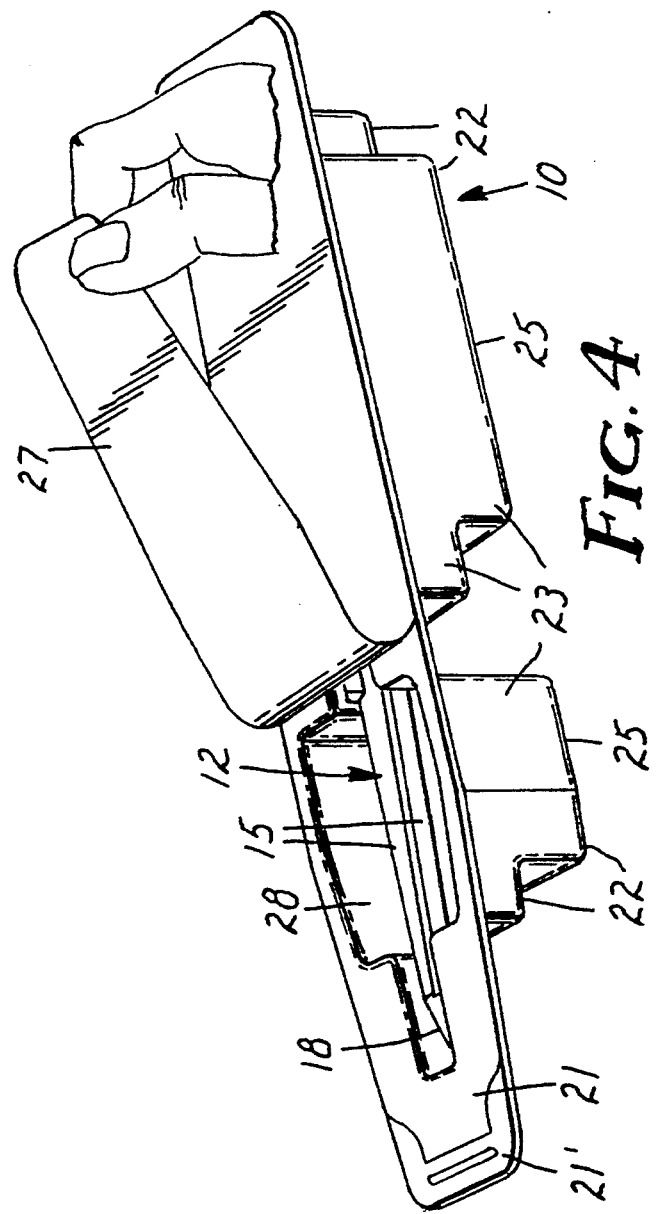
FIG. 4 is a reduced perspective view of the package and stapler of FIG. 1 in an assembled position and which illustrates a cover being manually peeled from the package.
Figure 5:
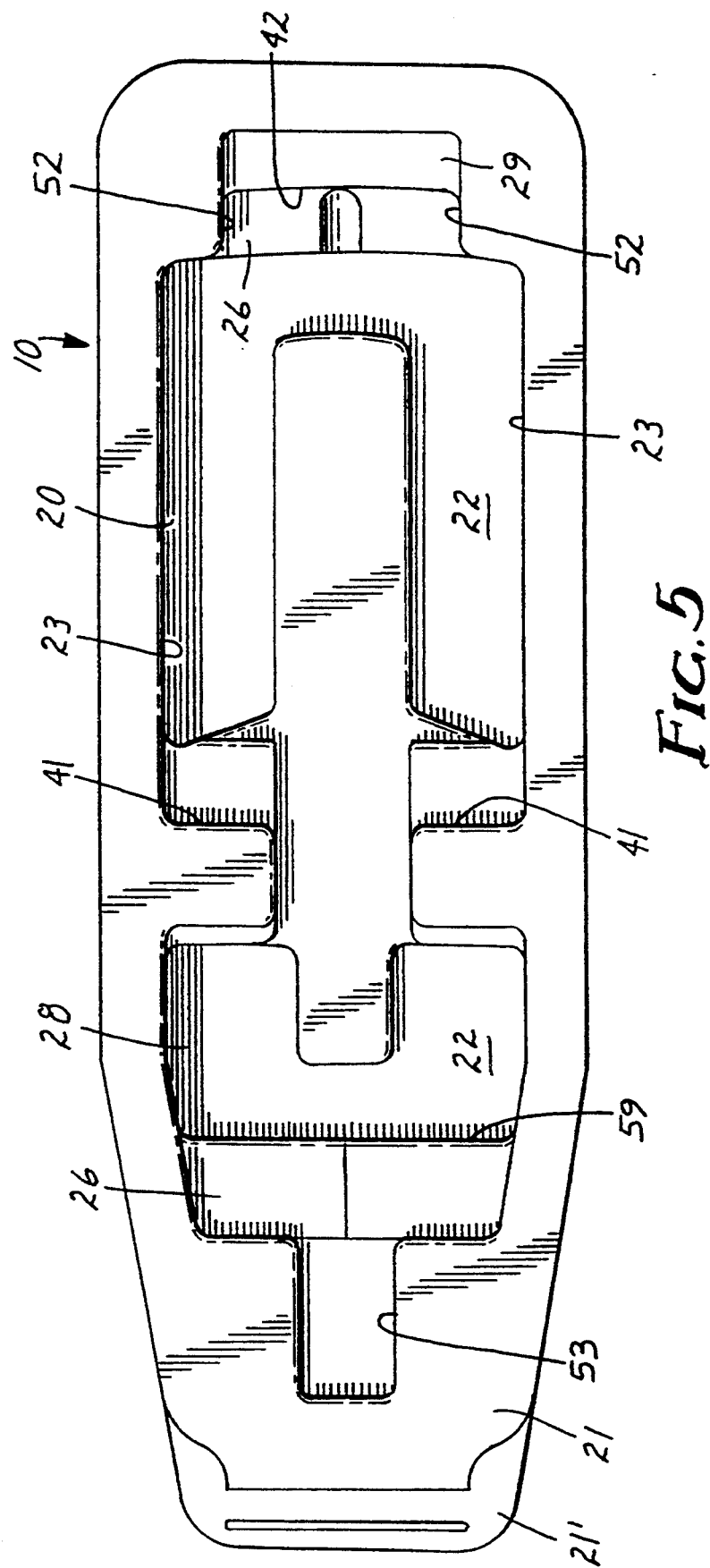
FIG. 5 is a top view of the package according to the present invention with the cover and stapler removed to illustrate details.

Additionally the package 10 includes a flexible cover 27 releasably attached to the top portion 21. The flexible cover 27 may be removed from the top portion 21 by being manually peeled from the top portion 21 as shown in FIG. 4. Once the cover 27 is removed or at least substantially removed from the top portion 21, the package 10 affords the user access to the stapler 12.

Preferably the flexible cover 27 is constructed from a heat sealable material and has the same general shape as the top portion 21. For example, a spun bond polyolefin fiber such as style 1073B TYVEK TM from Dupont of Wilmington, Del. may be used. Preferably, the flexible cover 27 is adhesively adhered to the top portion 21 along only the perimeter of the top portion by a hot melt or heat activated adhesive such as #18B Oliver TM clear adhesive coating generally available from Oliver Products of Grand Rapids, Mich. Optionally, materials such as laminated surgical paper or plastic film may be utilized. The flexible cover 27 may be heat sealed to the top portion 21 using an Alloyd Model 2Sm-1020 Heat Sealer (Alloyd Corporation, Chicago, Ill.) set at a temperature of 280–300 Fahrenheit, using 70–80 psi pressure and a dwell time of 2 to 3 seconds.

At one end of the top portion 21, the top portion 21 is depressed to a slightly lower level 21' which does not receive the heat activated adhesive (or alternatively heat from the heat sealer). Subsequently, the unattached end of the cover 27 can be used as a tab for assisting the tearing of the cover 27 from the top portion 21.

The package 10 also comprises a conformable member 30 situated between the cover 27 and the stapler 12 which deforms about the irregular surfaces of the stapler 12 to hold the stapler 12 relative to the package 10 when the cover 27 is attached to the top portion 21. As shown in FIG. 3, the conformable member 30 preferably conforms to the handle portion 14 of the stapler 12. Also, preferably, the conformable member 30 is resilient so that, when the cover 27 is attached to the top portion 21, the conformable member 30 biases the stapler 30 into contact with the abutment surface 26 to hold the stapler relative to the package 10.

Preferably, the cavity of the package 10 is free of structure for grasping stapler 12 (such as a detent portion present in some prior art packaging) other than the conformable member 30 so that, when the flexible cover 27 is removed and the package 10 is inverted, the stapler 12 may fall from the cavity under the influence of gravity without requiring the user to shake the package 10. Also, when the cavity is free of structure for grasping the stapler 12, the user is not required to firmly grasp the package 10 (and the top portion 21 which is not considered to be sterile) with the attendant risk of contamination.

As best seen in FIG. 1, the conformable member 30 comprises a generally rectangular shaped member having major surfaces 31 and planar end surfaces 32. Turning to FIG. 3, an end surface 32 of the conformable member 30 preferably abuts a button member 16 of the stapler 12. FIGS. 1 and 3 illustrate that the cavity has a portion 29 sized and shaped to receive a portion of the conformable member 30 to restrict movement of the conformable member 30 relative to the package 10.

The conformable member 30 preferably comprises a flexible, resilient, elastic foam material. The material should be capable of withstanding sterilization processes without having its material characteristics unduly compromised. The material should resist flaking or shedding of particulates into the cavity. For example, a closed cell cross-linked, low density polyethylene foam such as Plastazote ™, (generally available from J-Pac of Dover, N.H.) may be used as the conformable member. Another example is Voltec L200 available from Illbruck, Inc. of Minneapolis, Minn. Optionally, any suitable elastomer, plastic or rubber may be utilized.

The conformable member 30 preferably releases from contact with the stapler 12 when the cover 27 is removed from the top portion 21. Preferably, the conformable member 30 is attached to the cover 27 by means of an adhesive. The adhesive may comprise a heat activated adhesive or a pressure sensitive adhesive. For example, the conformable member may be attached to the cover 27 by the same hot melt adhesive used during the heat-sealing process which adheres the cover 27 to the top portion 21 of the package 10.

The conformable member 30 is preferably attached to the flexible cover 27 so that the conformable member 30 is removed from contact with the stapler 12 when the flexible cover 27 is removed from the top portion 21. Thus, opening the package comprises a one step procedure and time is not spent in retrieving loose elements from the package 10, and medical personnel are not required to touch the previously adhered top portion 21 with its attendant risk of contamination.

After the conformable member 30 and cover 27 are heat sealed, the completely sealed package 10 containing the enclosed stapler 12 is preferably then sterilized. Gamma radiation has been found to be an excellent sterilization technique for this type of packaging. The commonly known gamma radiation technique sterilizes the product and its local environment. The cover 27 is completely sealed around its periphery and, in conjunction with the bottom 21 top 22 and sidewall portions 23, acts as a barrier to contaminants of the stapler 12.

Optionally, ethylene oxide (ETO) gas sterilization may be used to sterilize the package and stapler 12. Tyvek ™ is permeable to ETO gas. Thus the gas penetrates into the package cavity and surrounds the instrument. After the requisite residence time the ETO gas is outgassed from the package resulting in a sterilized product.

TEST RESULTS

A preliminary test was conducted on a plurality of combinations of a stapler 12 and a package similar to the package 10, but which did not include the conformable member 30. The test was made in accordance with Project 1A of the National Safe Transit Association's (NSTA's) Preshipment Test Procedures which include the "Drop Test" for packaged products weighing between one (1) and twenty (20) pounds. The test included a drop from a height of about thirty (30) inches.

Each of the stapler 12 and package combinations failed the preliminary test. Failure was defined to include damage to the product, or premature movement of a part of the stapler (e.g. the firing knob 17), or a breach of the seal integrity (e.g. package puncture).

Next, one-hundred and fifty combinations of packages 10 and staplers 12 according to the present invention were tested in accordance with the procedures described in Project 1A of the National Safe Transit Association (NSTA) Preshipment Test Procedures, the entire contents of which are herein expressly incorporated by reference. Failure was defined in the same manner as in the preliminary tests. In view of the preliminary tests, it was surprising that none of the one-hundred and fifty combinations failed the tests.

The present invention has now been described with reference to several embodiments thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

What is claimed is:

1. A package for a surgical instrument comprising:
   a top portion,
   a bottom portion recessed from the top portion,
   sidewalls extending between the top portion and the bottom portion which define a cavity adapted to receive the surgical instrument, bearing surfaces adapted to abut the surgical instrument when the surgical instrument is placed in the cavity, a flexible cover releasably attached to the top portion, and adapted to be removed from the top portion by being manually peeled from the top portion to afford access to the surgical instrument, and a conformable member situated between the cover and the surgical instrument which deforms about at least a portion of the surgical instrument to hold the surgical instrument relative to the package when the cover is attached to the top portion.

2. A package according to claim i wherein the conformable member is attached to the flexible cover so that the conformable member releases from the surgical instrument when the cover is at least partially removed from the top portion.

3. A package according to claim 2 wherein the surgical instrument comprises a jaw portion and handle portion, and the sidewalls defining the cavity have a finger well portion generally adjacent the jaw portion of the surgical instrument when the surgical instrument is in the cavity to afford access to the surgical instrument.

4. A package according to claim 3 wherein the sidewalls defining the cavity include a finger well portion generally adjacent the handle portion of the surgical instrument when the surgical instrument is in the cavity to afford access to the surgical instrument.

5. A package according to claim 2 wherein the conformable member comprises a flexible, resilient material capable of being sterilized.

6. A package according to claim 5 wherein the conformable member comprises a foam material adapted to deform about the surgical instrument.

7. A package according to claim 1 wherein the conformable member is resilient and is attached to the flexible cover so that the conformable member is removed from contact with the surgical instrument when the flexible cover is removed from the top portion.

8. A package according to claim 1 wherein the top portion, bottom portion and sidewalls afford gamma radiation sterilization of the surgical instrument.

9. A package according to claim 1 wherein the top portion, bottom portion and sidewalls are an integral, monolithic, substantially transparent structure.

10. A package according to claim 1 wherein the flexible cover is heat sealed to the top portion and the conformable member is heat sealed to the flexible cover during the same heat sealing process.

11. A package according to claim 1 wherein the package is free of structure for grasping surgical instrument other than the conformable member so that, when the flexible cover is removed and the package is inverted, the surgical instrument is capable of falling from the cavity under the influence of gravity without requiring shaking of the package or firm manual grasping of the package.

12. A package according to claim 1 wherein the surgical instrument comprises jaw and handle portions and an imaginary longitudinal axis, the bottom portion has generally planar exterior base surfaces for resting on a horizontal plane such as a table, and wherein, the bearing surfaces situate the stapler such that the longitudinal axis of the stapler is inclined relative to base surfaces to facilitate grasping of the jaw portion of the stapler.

13. A package according to claim 1 wherein the cavity has a portion sized and shaped to receive a portion of the conformable member to restrict movement of the conformable member relative to the package.

14. A package according to claim 1 wherein the surgical instrument comprises a surgical instrument with a relatively large mass.

15. A package according to claim 14 wherein the surgical instrument weighs between about one-quarter ($\frac{1}{4}$) and about one-hundred (100) pounds.

16. A package according to claim 1 wherein the surgical instrument comprises relatively movable parts and the package comprises means for restricting movement of the movable parts.

17. In combination, a sterile surgical stapler comprising a handle portion and a jaw portion, and a sterile package comprising:

a top portion, a bottom portion recessed from the top portion, sidewalls extending between the top portion and the bottom portion which define a cavity that receives the stapler, bearing surfaces abutting the stapler, a flexible cover releasably attached to the top portion, and adapted to be removed from the top portion by being manually peeled from the top portion to afford access to the stapler, and a conformable member situated between the cover and the stapler which deforms about at least a portion of the stapler to hold the stapler relative to the package.

18. A combination according to claim 17 wherein the conformable member is adapted to release from the stapler when the cover is at least partially removed from the top portion, and the stapler comprises button members on the handle portion, the conformable member comprises a flexible, resilient, generally rectangular shaped member having major surfaces and planar end surfaces, and an end surface of the conformable member abuts a button member.

19. A combination according to claim 17 wherein the sidewalls defining the cavity have finger well portions generally adjacent the jaw and handle portions of the stapler to afford access to the stapler when the cover is removed.

20. A combination according to claim 17 wherein the conformable member comprises a flexible, resilient foam material capable of being sterilized and adapted to deform about the stapler.

21. A combination according to claim 17 wherein the conformable member is attached to the flexible cover so that the conformable member is removed from contact with the stapler when the flexible cover is removed from the top portion.

22. A combination according to claim 17 wherein the top portion, bottom portion and sidewalls are capable of affording gamma radiation sterilization of the stapler, the top portion, bottom portion and sidewalls are an integral, monolithic structure, and the flexible cover is heat sealed to the top portion.

23. A combination according to claim 17 wherein the package is free of structure for grasping stapler other than the conformable member so that, when the flexible cover is removed and the package is inverted, the stapler is capable of falling from the cavity under the influence of gravity without requiring shaking of the package or manual grasping of the stapler.

24. A combination according to claim 17 wherein the stapler comprises an imaginary longitudinal axis, the bottom portion has generally planar, exterior base surfaces for resting on a horizontal plane such as a table, and wherein, the bearing surfaces situate the stapler such that the longitudinal axis of the stapler is inclined relative to base surfaces to facilitate grasping of the jaw portion of the stapler.

* * * * *